United States Patent
Kreuter

(10) Patent No.: US 7,914,827 B2
(45) Date of Patent: Mar. 29, 2011

(54) USE OF EXTRACTS OR EXTRACTANTS OF THE GUAJACUM TYPES, SAID EXTRACTS OR EXTRACTANTS BRINGING ABOUT PHOSPHODIESTERASE-4 INHIBITION AND METHOD FOR PRODUCING THE SAME

(75) Inventor: Matthias-Heinrich Kreuter, Walenstadt (CH)

(73) Assignee: Max Zeller Soehne AG, Romanshorn (CH)

( * ) Notice: Subject to any disclaimer, the term of this patent is extended or adjusted under 35 U.S.C. 154(b) by 42 days.

(21) Appl. No.: 12/227,596

(22) PCT Filed: Jul. 4, 2007

(86) PCT No.: PCT/CH2007/000325
§ 371 (c)(1),
(2), (4) Date: Nov. 21, 2008

(87) PCT Pub. No.: WO2008/003185
PCT Pub. Date: Jan. 10, 2008

(65) Prior Publication Data
US 2009/0142423 A1    Jun. 4, 2009

(30) Foreign Application Priority Data

Jul. 5, 2006 (CH) ..................................... 1076/06

(51) Int. Cl.
*A61K 36/00* (2006.01)
(52) U.S. Cl. ....................................................... 424/725
(58) Field of Classification Search ........................ None
See application file for complete search history.

(56) References Cited

U.S. PATENT DOCUMENTS

2003/0055007 A1* 3/2003 Sakuma .......................... 514/22
* cited by examiner

*Primary Examiner* — Susan C Hoffman
(74) *Attorney, Agent, or Firm* — The Nath Law Group

(57) ABSTRACT

The present invention relates to the use of extracts or extractants of the guajacum types, said extracts or extractants bringing about phosphodiesterase-4 inhibition, and to a method for producing the same.

21 Claims, No Drawings

USE OF EXTRACTS OR EXTRACTANTS OF THE GUAJACUM TYPES, SAID EXTRACTS OR EXTRACTANTS BRINGING ABOUT PHOSPHODIESTERASE-4 INHIBITION AND METHOD FOR PRODUCING THE SAME

The present invention relates to the use of extracts or extract substances from *Guajacum* species, wherein said extracts or said extract substances effect a phosphodiesterase-4 inhibition as well as a method for their preparation.

For example, uses of *Guajacum* preparations are described in HagerROM 2002, Springer publishing company, Heidelberg. In this document popular applications such as the treatment of gout, rheumatism, syphilis and an unspecified skin disease are mentioned.

In the field of homeopathy the monograph for preparation of commission D in the Bundesanzeiger no. 190 of Oct. 10, 1985 mentions tonsillitis and throat inflammations, inflammations of bronchi and lungs, rheumatism and gout as applications in accordance with the homeopathic drug concept.

As a drug the resin obtained by melt out from the heartwood of *Guajacum officinale* L. and *Guajacum sanctum* L. is used. Said resin serves for manufacturing preparations that are based on a mother tincture and liquid dilutions according to HAB 1.

A monograph for allopathic preparation of commission E is based on *Guajacum* wood as published in Bundesanzeiger 76 of Apr. 23, 1987. As indication the supportive treatment of rheumatic medical conditions is mentioned.

In DE 101 31 036 A1 an elixir is described comprising per 100 g 70 g of an alcoholic mazerate preparation (15% ethanol by volume) made of 50 g Condurango bark, 0.60 g *Guajacum* wood, 0.40 g dandelion root with leaves and 0.40 g peppermint leaves.

According to the opinion of the inventor it should mainly be the undefined ingredients of the Condurango bark as well as undefined ingredients of *Guajacum* wood that contributes to the reduction of the virus load in HIV. Data for lowering the virus load in HIV is not provided. From the application's description the skilled person cannot derive how this inventor came to his conclusion.

In U.S. Pat. No. 4,774,229 a method for treating skin tumours of mammals is claimed. In this method the tumours are treated topically with a novel mixture of a plant extract of the family Zygophyllaceae and non-alkaline metal halide. Furthermore, in column 5, lines 2 to 10 it is described that this mixture should be effective against brain tumours, breast tumours and further types of tumours. From the examples 1 to 6 of U.S. Pat. No. 4,774,229 it is obvious for the skilled person that initially a pheonolic extract is prepared from the plant material, which is subsequently contacted with a metal halide resulting in novel compounds, i.e. complexes of phenolic compounds and metal ions. Obviously, the basic concept of this invention is to convert the salts of antimony, cadmium, copper and zinc being highly cytotoxic depending on their concentration into complexes with phenolic compounds in order to make them more applicable for the desired uses.

In the context of a development project a dry extract of plant parts of *Guajacum* was to be prepared, that was to be suitable for the supportive treatment of rheumatic disorders in accord with the monograph of commission E. For this purpose a number of fluid extracts were prepared. The preparation of the fluid extract did not involve any difficulties. However, the obtained fluid extracts could not be transformed into spissum extracts by standard procedures, because upon concentration massive precipitations and tar-like deposits were formed. Moreover, the addition of various excipients such as maltodextrin, mannitol, lactose, tricalcium phosphate, gum Karaya and gum arabicum to the fluid extract did not prevent said massive precipitations and tar-like deposits. Neither the preparation of a spissum extract nor a dry extract were to be realized in this manner in accordance with good manufacturing practice (GMP).

It is the objective of the present invention to provide a method for preparing a dry extract from *Guajacum* species, in particular those selected from the group consisting of *Guajacum sanctum* L., *Guajacum officinale* L., *Guajacum coulteri* Gray and *Guajacum parvifolium* Planch.

The invention is characterized by the features of the independent claims. Preferred embodiments are defined in the dependent claims.

Surprisingly, it was found that the massive precipitations and tar-like deposits occurring during the above-mentioned concentration can be prevented completely, if the obtained alcoholic or aqueous alcoholic fluid extract is added to an aqueous solution of gum arabicum in a controlled (dosed) manner and concentrated in a controlled manner in a vacuum evaporator. When doing this, said addition and said concentration must be effected in such a way that during this process an alcohol and water concentration is maintained, so that neither the gum arabicum nor the plant extract substances contained in the extract precipitate.

This completely unexpected effect can now be explained because an excess of gum arabicum relative to the extract substances dissolved in the fluid extract must exist, gum arabicum principally being capable of forming quasi-emulsions and stable suspensions in aqueous media as well as aqueous media with low alcoholic content.

A homogenous spissum extract results, which has neither deposits nor phase separations and which can be converted directly or subsequent to a further concentration step into a dry extract. The dry extract can be obtained by conventional spray drying, belt drying or blade drying of the spissum extract, in particular of the further concentrated spissum extract.

The fluid extract, as well as the dry extract prepared therefrom, were assayed in various pharmacological in vitro test systems. In these tests a fluid extract prepared with 80% m/m ethanol proved itself as a moderate inhibitor of cyclooxygenase 1. The $IC_{50}$ value for COX1 was 30 μg/ml. The human leukocyte elastase HLE was inhibited by 50% at 60 μg/ml. The release of interleukin 1-β from human macrophages was inhibited by 50% at 45 μg/ml. The release of interleukin 6 was inhibited by 50% at 7 μg/ml. The release of tumour necrosis factor α was inhibited by 50% at 7 μg/ml. Interestingly, the fluid extract as well as the dry extract obtained thereof both inhibit the leucotriene synthesis in a granulocyte based 5-lipoxygenase test system at significantly lower concentrations in comparison to the above test systems. $IC_{50}$ values of 0.5 μg/ml were obtained.

Surprisingly, it was found out that the dry extract prepared according to the method of the invention inhibited human phosphodiesterase-4, abbreviated PDE4, in a pharmacological in vitro test system with an $IC_{50}$ value of 0.2 μg/ml.

Because of these results the dry extract prepared according to the method of the invention was further assayed in a pharmacological in vitro test system of human phosphodiesterase-5, abbreviated PDE %, in order to determine whether the extract has a specificity for one of the phosphodiesterases. An inhibition with an $IC_{50}$ value of 1.5 μg/ml was found.

This striking difference in the intensity of the inhibitory effect of the extract leads to the conclusion of a pronounced specificity of the extract for phosphodiesterase-4.

Hence, it was surprisingly found that dry extracts prepared according to the invention inhibit phosphodiesterase-4 and obviously contain at least one extract substance that inhibits phosphodiesterase-4. In comparison to the above-mentioned other pharmacological in vitro test systems this inhibition takes place at a significantly lower $IC_{50}$ value.

When considering the present pharmacological and clinical reports obtained with synthetic PDE4 inhibitors, for example Rolipram, it becomes clear that the inhibition of phosphodiesterase-4 will have great relevance for the therapy of a whole lot of partly serious illnesses. In this respect the review article of M. D. Housley, P. Schafer and K. Y. J Zhang, Drug Discovery Today, vol. 10, no. 22, November 2005, pages 1503-1509 is noted. In this article exclusively those active substances are mentioned that comprise at least one nitrogen atom.

The following examples illustrate the present invention.

EXAMPLE 1

6.5 kg heart wood with a low content of sap wood with a cutting size of about 1 mm to about 2 mm of *Guajacum sanctum* L. were extracted at a temperature of between 30° C. and 45° C. over 2 hours with a mixture of 80 parts by weight ethanol and 20 parts by weight water while stirring. The weight ratio of drug to extraction agent mixture was 1:7. The drug extracted in this manner was separated by means of layer filtration.

In an evaporator 300 g gum arabicum were dissolved in 1.7 kg water at a temperature of 30° C. while stirring resulting in a solution of 15% m/m gum arabicum. To this solution of gum arabicum initially 1.2 kg of the above-obtained fluid extract were added and concentrating in vacuo (300 mbar to 20 mbar) and at elevated temperature was initiated. Directly after beginning the distillation the remaining part of the fluid extract was continually added into the evaporator in a controlled manner (dosed) until the complete amount of the fluid extract was retracted and concentrated. During the concentration of the mixture a concentration of ethanol of between 15 and 35% m/m was maintained by means of controlled addition of the fluid extract or, if necessary, water until the obtained spissum extract had reached a dry substance content of 30 to 40% m/m.

During the preparation of the spissum extract the homogeneity of the concentrating mixture was monitored visually. The spissum extract obtained in this manner had a light brown colour, was free-flowing and of homogenous consistency.

This spissum extract was further concentrated in vacuo (300 mbar to 20 mbar) and at an elevated temperature (40° C. to 55° C.) until a dry substance content of 45% to 55% was reached. The further concentrated spissum extract (2 kg with a dry substance content of 50%) had a light brown colour, was thick-flowing and of homogenous consistency. This further concentrated spissum extract was dried in a dryer in vacuo at a pressure of 150 mbar to 10 mbar and at a temperature of 40° C. to 55° C. 1 kg of a light brown dry extract with a content of 30% m/m of gum arabicum excipient was obtained.

EXAMPLE 2

With a dry extract obtained in analogy to example 1 a PDE4 assay was performed in accordance with the following literature citations:

Method for Isolating PDE4 from U937 Cells:

Torphy T. J., Zhou H. L., Cieslinski L. B. (1992), "Stimulation of beta adrenoreceptors in a human monocyte cell line (U937) up-regulates cyclic AMP-specific phosphodiesterase activity", J. Pharamcol. Exp. Ther. 263 (3), pages 1195-1205.

Method for Identifying PDE: for PDE4-$^3$H-cAMP as Tracer

Schilling R. J., Morgan D. R. and Kilpatrick B. F. (1994) "A high throughput assay for cyclic nucleotide phosphodiesterases", Anal. Biochem. 216, pages 154-158.

The dried extract prepared according to the present invention was dissolved in 90% v/v ethanol and diluted so that a maximum concentration of 1% v/v ethanol in the test system resulted. The extract dissolved in this manner was assayed for its inhibitory activity in the following concentrations calculated on the basis of the extract without excipient:

| Concentration [µg/ml] | Inhibitory activity [%] |
|---|---|
| 0.1 | 39 |
| 0.3 | 58 |
| 1.0 | 78 |
| 3.0 | 90 |
| 10.0 | ≧95 |

Hence, for the assayed dried extract prepared according to the invention an $IC_{50}$ value of 0.2 µg/ml resulted.

As control substance Rolipram, a PDE4 specific inhibitor, was assayed for its inhibitory activity in the following concentrations in comparison.

| Concentration [µg/ml] | Inhibitory activity [%] |
|---|---|
| 0.01 | 6 |
| 0.1 | 24 |
| 1.0 | 56 |
| 10.0 | 66 |
| 100.0 | 79 |

Hence, for the assayed control substance Rolipram an $IC_{50}$ value of 0.8 µg/ml resulted.

EXAMPLE 3

With a dry extract obtained in analogy to example 1 a PDE5 assay was performed in accordance with the following literature citations:

Method for Isolating PDE5:

Mullershausen F., Friebe A., Feil R., Thompson W. J., Hofmann F., Koesling D. (2003) "Direct activation of PDE5 by cGMP: long-term effects within NO/cGMP signalling", J. of Cell Biology 160: (5), pages 719-727.

Method for Identifying PDE: for PDE5-$^3$H-cGMP as Tracer

Schilling R. J., Morgan D. R. and Kilpatrick B. F. (1994) "A high throughput assay for cyclic nucleotide phosphodiesterases", Anal. Biochem. 216, pages 154-158.

The dried extract prepared according to the present invention was dissolved in 90% v/v ethanol and diluted so that a maximum concentration of 1% v/v ethanol in the test system resulted. The extract dissolved in this manner was assayed for its inhibitory activity in the following concentrations calculated on the basis of the extract without excipient:

| Concentration [µg/ml] | Inhibitory activity [%] |
| --- | --- |
| 0.1 | 5 |
| 0.3 | 26 |
| 1.0 | 48 |
| 3.0 | 69 |
| 10.0 | 86 |

Hence, for the assayed dried extract prepared according to the invention an $IC_{50}$ value of 1.5 µg/ml resulted.

As control substance Sildenafil, a PDE5 specific inhibitor, was assayed in the following concentrations for its inhibitory activity in comparison.

| Concentration [nM] | Inhibitory activity [%] |
| --- | --- |
| 0.001 | 5 |
| 0.1 | 21 |
| 10.0 | 52 |
| 1000.0 | 74 |

Hence, for the assayed control substance Sildenafil an $IC_{50}$ value of 8 nM resulted.

Because of the results presented in examples 2 and 3 it can be concluded that the dry extract prepared according to the invention or at least one extract substance comprised therein is suitable for use in the treatment of diseases, wherein a phosphodiesterase-4 inhibition is desired and effective.

The invention claimed is:

1. A method for preparing a dry extract from a plant of *Guajacum* species comprising:
    extracting one or more of *Guajacum* species selected from the group consisting of *Guajacum sanctum* L., *Guajacum officinale* L., *Guajacum coulteri* Gray and *Guajacum parvifolium* Planch, with a mixture of at least one alcohol and water,
    adding the obtained fluid extract to an aqueous solution of arabic gum in a controlled manner and concentrating the extract in a controlled manner such that neither the arabic gum nor the plant extract substance percipitates, and
    drying the obtained spissum extract,
wherein the alcohol is an alcohol with 1 to 5 carbon atoms.

2. The method of claim 1, wherein the obtained spissum extract is further concentrated before the drying.

3. The method of claim 1, wherein a heartwood or a mixture of heart wood and sapwood of the plant is extracted in ground or cut form.

4. The method of claim 3, wherein the cut form has a cut size of about 1 mm to about 2 mm.

5. The method of claim 1, wherein the mixture of at least one alcohol and water consists of 30 to 90 m/m % alcohol and 70 to 10 m/m % water.

6. The method of claim 5, wherein the alcohol is ethanol.

7. The method of claim 5, wherein the mixture consists of 75 to 85 m/m % of alcohol and 25 to 15 m/m % of water.

8. The method of claim 1, wherein 1 to 20 parts by weight of solvent are employed per part by weight of the plant to be extracted.

9. The method of claim 8, wherein the solvent is 6 to 12 parts by weight per part by weight of the plant.

10. The method of claim 1, wherein the extraction is effected at a temperature of 30° C. to 50° C. and for a time period of 2 to 4 hours.

11. The method of claim 1, wherein 0.2 to 0.6 parts by weight of arabic gum are employed per part by weight of extracted substance.

12. The method of claim 1, wherein an aqueous solution of 10 to 30 m/m % arabic gum is initially provided.

13. The method of claim 12, wherein 0.4 parts by weight of arabic gum are employed per part by weight of extracted substance.

14. The method of claim 12, wherein the aqueous solution is 15 m/m %.

15. The method of claim 1, wherein an alcohol concentration of between 15 and 35 m/m % is present while concentrating the mixture and that this concentration is maintained until a content of dry substance of 30 to 40 m/m % is reached in the spissum extract.

16. The method of claim 15, wherein the alcohol concentration is 25 m/m %.

17. The method of claim 2, wherein the obtained spissum extract is further concentrated to an alcohol concentration of between 0 and 10 m/m %.

18. The method according to claim 1, wherein the dry extract is obtained by spray drying, belt drying or blade drying of the spissum extract.

19. The method of claim 18, wherein the obtained spissum extract is further concentrated to an alcohol concentration of 5 m/m %.

20. The method according to claim 2, wherein the dry extract is obtained by spray drying, belt drying or blade drying of the further concentrated spissum extract.

21. The method of claim 1, wherein the dry extract is free of nordihydroguajaretic acid (NDGA).

\* \* \* \* \*

UNITED STATES PATENT AND TRADEMARK OFFICE
CERTIFICATE OF CORRECTION

| | | |
|---|---|---|
| PATENT NO. | : 7,914,827 B2 | Page 1 of 1 |
| APPLICATION NO. | : 12/227596 | |
| DATED | : March 29, 2011 | |
| INVENTOR(S) | : Matthias-Heinrich Kreuter | |

It is certified that error appears in the above-identified patent and that said Letters Patent is hereby corrected as shown below:

Column 6, Claim 14, Line 26
Please delete "is 15 m/m %." and replace with -- is 15 m/m% arabic gum. --

Signed and Sealed this
Tenth Day of May, 2011

David J. Kappos
*Director of the United States Patent and Trademark Office*